(12) United States Patent
Satyavolu et al.

(10) Patent No.: US 10,407,453 B2
(45) Date of Patent: Sep. 10, 2019

(54) PROCESS FOR ISOLATING C5 SUGARS FROM BIOMASS HYDROLYZATE

(71) Applicant: University of Louisville Research Foundation, Inc., Louisville, KY (US)

(72) Inventors: Jagannadh Satyavolu, Louisville, KY (US); Sadakatali S. Gori, Louisville, KY (US); Michael H. Nantz, Louisville, KY (US); Mandapati V. Ramakrishnam Raju, Louisville, KY (US); Christopher T. Burns, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 17 days.

(21) Appl. No.: 15/093,005

(22) Filed: Apr. 7, 2016

(65) Prior Publication Data

US 2016/0297845 A1     Oct. 13, 2016

Related U.S. Application Data

(60) Provisional application No. 62/144,104, filed on Apr. 7, 2015.

(51) Int. Cl.
    *C07H 3/02*     (2006.01)
    *C07H 1/08*     (2006.01)

(52) U.S. Cl.
    CPC ............... *C07H 3/02* (2013.01); *C07H 1/08* (2013.01); *Y02E 50/343* (2013.01)

(58) Field of Classification Search
    CPC .................................. C07H 3/02; C07H 1/08
    USPC ............................................. 127/37; 536/127
    See application file for complete search history.

(56) References Cited

U.S. PATENT DOCUMENTS

| 3,586,537 | A | 6/1971 | Starrkirclr et al. |
| 7,572,376 | B2 * | 8/2009 | Baniel ............... B01D 11/0446 |
| | | | 210/634 |

OTHER PUBLICATIONS

Duggan et al. Boron acids as protective agents and catalysts in synthesis. J. Chem. Soc., Perkin Trans. 1:1325-1339, 2002. (Year: 2002).*
EXXAL 10 ALCOHOL, Product Safety Summary, ExxonMobil Chemical, Mar. 2016. (Year: 2016).*
ShellSol 2046 NA, Technical Datasheet, Shell Chemicals, Mar. 2016. (Year: 2016).*
Liu et al. Isolation and Characterization of Cellulose Obtained from Ultrasonic Irradiated Sugarcane Bagasse. J. Agric. Food Chem. 54:5742-5748, 2006. (Year: 2006).*
Lloyd, T., et al. Combined sugar yields for dilute sulfuric acid pretreatment of corn stover followed by enzymatic hydrolysis of the remaining solids. Bioresource Technology 2005, 96, (18), 1967-1977.

(Continued)

*Primary Examiner* — Yih-Horng Shiao
(74) *Attorney, Agent, or Firm* — Jenkins, Wilson, Taylor & Hunt, P.A.

(57) ABSTRACT

Provided are processes for isolating hemicellulose-based sugar from a biomass. The process includes providing a biomass hydrolyzate including a C5 sugar, forming a boronic ester or diester of the C5 sugar, extracting the boronic ester of diester of the C5 sugar, precipitating the C5 sugar using a boron capture agent, and isolating the C5 sugar from the precipitate. The isolated C5 sugar is provided in dry form.

19 Claims, 6 Drawing Sheets

(56) References Cited

OTHER PUBLICATIONS

Torget, R., et al. Dilute Sulfuric-Acid Pretreatment of Hardwood Bark. Bioresource Technology 1991, 35, (3), 239-246.
Lee, J.W., et al. Efficiencies of acid catalysts in the hydrolysis of lignocellulosic biomass over a range of combined severity factors. Bioresource Technology 2011, 102, (10), 5884-5890.
Fonseca, D.A., et al. Towards Integrated Biorefinery from Dried Distillers Grains: Selective Extraction of Pentoses using Dilute Acid Hydrolysis. Accepted for publication in Biomass and Bioenergy 2014.
Lupitsky, R., et al. Towards Integrated Refinery from Dried Distillers Grains: Evaluation of Feed Application for Co-products. Accepted for publication in Biomass and Bioenergy 2014.
Rafiqul, I.S.M., et al. Design of process parameters for the production of xylose from wood sawdust. Chemical Engineering Research & Design 2012, 90, (9), 1307-1312.
Tortosa, C.I.G., et al. An Economic-Process for Preparation of Xylose and Derivatives by Hydrolysis of Corn Cobs. Biological Wastes 1990, 33, (4), 275-286.
Herrera, A., et al. Production of xylose from sorghum straw using hydrochloric acid. Journal of Cereal Science 2003, 37, (3), 267-274.
Reichvilser, M.M. et al. Boronic acid mono- and diesters of the aldopentoses. Carbohydrate Research 2010, 345, (4), 498-502.
Roy, C.D., et al. A comparative study of the relative stability of representative chiral and achiral boronic esters employing transesterification. Monatshefte Fur Chemie 2007, 138, (9), 879-887.
Roy, C.D., et al. Stability of boronic esters—Structural effects on the relative rates of transesterification of 2-(phenyl)-1,3,2-dioxaborolane. Journal of Organometallic Chemistry 2007, 692, (4), 784-790.
Kaupp, G., et al. Waste-free and facile solid-state protection of diamines, anthranilic acid, dials, and polyols with phenylboronic acid. Chemistry—a European Journal 2003, 9, (17), 4156-4160.
Sun, J., et al. A Method for the Deprotection of Alkylpinacolyl Boronate Esters. Journal of Organic Chemistry 2011, 76, (9), 3571-3575.
Matteson, D.S., et al. Hydrolysis of substituted 1,3,2-dioxaborolanes and an asymmetric synthesis of a differentially protected syn,syn-3-methyl-2,4-hexanediol. Journal of Organic Chemistry 1996, 61, (17), 6047-6051.
Kabay, N., et al. Boron in seawater and methods for its separation—A review. Desalination 2010, 261, (3), 212-217.
Bull, S.D., et al. Exploiting the Reversible Covalent Bonding of Boronic Acids: Recognition, Sensing, and Assembly. Accounts of Chemical Research 2013, 46, (2), 312-326.
Carboni, B., et al. Boronic ester as a linker system for solid phase synthesis. Tetrahedron Letters 1999, 40, (45), 7979-7983.
Grohmann, K., et al. Optimization of dilute acid pretreatment of biomass. Seventh Symp. Biatechnol. Fuels Chem. 1985, 15, 59-80.
Griffin, G.J., et al. Solvent extraction and purification of sugars from hemicellulose hydrolysates using boronic acid carriers. J Chem Technol Biotechnol (2004) 0268-2575.
Li, B., et al. High yield aldose-ketose transformation for isolation and facile conversion of biomass sugar to furan. Green Chem. (2013) 15, 2149-2157.

\* cited by examiner

PROCESS FOR ISOLATING C5 SUGARS FROM BIOMASS HYDROLYZATE

RELATED APPLICATIONS

This application claims priority from U.S. Provisional Application Ser. No. 62/144,104, filed Apr. 7, 2015, the entire disclosure of which is incorporated herein by this reference.

TECHNICAL FIELD

The presently-disclosed subject matter relates to a process for isolating a C5 sugar from a biomass hydrolyzate. In particular, the presently-disclosed subject matter relates to a process for isolating a C5 sugar, such as xylose, from a biomass hydrolyzate that makes use of a precipitation protocol to deliver the C5 sugar in a form suitable for subsequent synthetic transformations, such as the production of a C5-platform of biochemical and biofuels.

BACKGROUND

Utilizing renewable resources such as co-products from grain processing to produce a C5-platform of biochemical and biofuels is advantageous from the perspective of the environment, process integration and economics, as well as energy independence and national security. Those co-products are richer in hemicelluloses and the C5 sugars derived from those co-products can be converted via chemical synthesis routes to higher-value bio-jet fuels and high energy density components of bio-jet fuels.

Hemicellulose-based sugars (e.g., xylose and arabinose) can be a platform for synthesis of a variety of industrially important chemicals that are currently derived from petroleum. Pentoses were identified by the U.S. Department of Energy in 2004 among the top candidates of valuable chemical precursors that could be produced from biomass. While numerous studies have been performed to develop processes for extraction of monosaccharides from a wide range of biomass feedstocks, these monosaccharide extraction processes have been developed as pretreatment processes to improve the downstream processes—not necessarily to isolate and use pentose sugars from the biomass feedstocks. For example, various hydrolytic techniques, such as steam explosion, steam explosion with dilute sulfuric acid, organosolv extraction, and biological treatment with white rot fungi, have all been extensively investigated as pretreatment methods to obtain hydrolyzates rich in monosaccharides.

However, the sugar concentrations in the resulting hydrolyzates are typically still lower than desired for downstream processing. As such, hydrolyzate concentration is often required before conversion to value-added chemicals or biofuels. These concentration steps may deteriorate the sugars and many of the sugar degradation compounds are toxic to the fermentation process, severely limiting yields and effectiveness of the overall processes. To address these drawbacks, one hydrolyzate treatment approach relies upon lipophilic boronic acids to form boronate complexes with cis-diol moieties of sugars, which are extracted into an organic phase by ion pairing with lipophilic quaternary ammonium cations. The resulting salts are then hydrolyzed in a clean, aqueous acidic solution to regenerate the sugars for use in subsequent fermentation or other enzymatic processes. Although this approach extracts sugars from the hydrolyzate, the utility of the extracted sugars is limited, as the aqueous sugar solution is not compatible with many biofuel or biochemical conversion schemes that require the sugars to be in dry form.

Accordingly, there remains a need in the art for a process of isolating C5 sugars, such as xylose, from hydrolyzates in a manner that allows the C5 sugars to then be converted and/or used in the production of a C5-platform of biochemical and biofuels.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods for the extraction of hemicellulose-based sugars from a biomass hydrolyzate. In some embodiments, the process includes providing a biomass hydrolyzate including a C5 sugar, forming a boronic ester or diester of the C5 sugar, extracting the boronic ester of diester of the C5 sugar, precipitating the C5 sugar using a boron capture agent, and isolating the C5 sugar from the precipitate. In some embodiments, the isolated C5 sugar is provided in dry form. In some embodiments, the processes described herein also include recovering one or more reagents used in the isolation of the C5 sugar.

DESCRIPTION OF EXEMPLARY EMBODIMENTS

Figure 1:
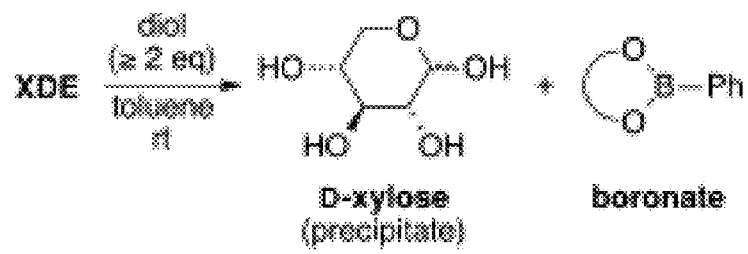
FIG. 1 is a process view of the transesterification of XDE using diols; XDE=xylose di-ester $(PhB)_2(D\text{-}XylfH_{-4})$.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as is commonly understood by one of skill in the art to which the invention(s) belong. All patents, patent applications, published applications and publications, databases, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it understood that such identifiers can change and particular information on the internet can come and go, but equivalent information can be found by searching the internet.

Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is based, at least in part, on the development and demonstration of an integrated C5-based biorefinery concept to extract and isolate C5 sugars for the purpose of converting them to a C5-platform of biochemical and biofuels, such as bicyclopentane (BCP). In this process and, at least in part, for economic reasons, a hemicellulose rich "captive" agricultural biomass is used to selectively extract C5 sugars. As such, in some embodiments, a process for isolating a C5-rich biomass is provided that includes an initial step of providing a biomass hydrolyzate including a C5 sugar, such as what is present in a hemicellulose-rich biomass.

As would be understood by those skilled in the art, the terms "cellulose" and "hemicellulose" are used herein to refer to organic compounds present in almost all plant cells wall. "Cellulose" is generally used to refer to an organic compound with the formula $(C_6H_{10}O_6)n$ that forms a polysaccharide consisting of a linear chain of several hundred to many thousands of β(1→4) linked D-glucose units. In contrast to cellulose, the term "hemicellulose" is used herein to refer to any of several heteropolymers or matrix polysaccharides that are present along with cellulose in almost all plant cell walls. Indeed, by weight, the largest component of plant matter is lignocellulosic material; a mixture of cellulose, hemicellulose, and lignin. When these materials are subjected to either acid or enzymatic hydrolysis to divide the molecules into their constituent sugars, the hemicellulose breaks down to form five-carbon or C5 sugars, such as xylose, whereas the cellulose chain splits into glucose (a six carbon sugar or "C6 sugar").

In this regard, the terms "C6 sugar" or "hexose" are used interchangeably herein to refer to monosaccharides that include six carbon atoms, typically have the chemical formula $C_6H_{12}O_6$, and are classified according to their functional groups, with aldohexoses having an aldehyde at position 1 of the C6 sugar, and ketohexoses having a ketone at position 2 of the C6 sugar. The terms "C5 sugar" or "pentose," on the other hand, are used interchangeably herein to refer to monosaccharides that include five carbon atoms, and that can be generally organized into two groups, namely aldopentoses, which have an aldehyde functional group at position 1 of the C5 sugar, and ketopentoses, which have a ketone functional group in position 2 or 3 of the C5 sugar.

To produce a C5-rich biomass hydrolyzate or, in other words, a C5-rich biomass subjected to hydrolysis, hemicellulose-rich materials are typically first provided. Suitable hemicellulose-rich materials and/or hemicellulose-rich agricultural biomasses include any material and/or agricultural biomass having a hemicellulose concentration of at least 10%, at least 15%, at least 20%, at least 25%, at least 30%, between 10% and 99%, between 10% and 90%, between 15% and 75%, between 15% and 50%, or any combination, sub-combination, range, or sub-range thereof. Exemplary hemicellulose-rich agricultural biomasses that can be used in this regard include, but are not limited to: soy hulls from soybean processing, rice hulls from rice milling, corn fiber from wet milling or dry milling, bagasse from sugarcane processing, pulp from sugar beets processing, distillers grains, and the like.

Upon providing the hemicellulose rich biomass, in some embodiments, to ensure an effective amount of C5 sugars are isolated from the biomass in subsequent hydrolysis steps, the biomass is first subjected to a pretreatment procedure.

The pretreatment procedure, performed prior to hydrolysis, provides a pretreated biomass having an enriched fiber fraction (i.e., enhances the fiber value of the biomass). For example, in some embodiments, the pretreatment procedure includes a screening procedure that makes use of a sieve (e.g., a sieve with 0.85 mm openings) to produce a coarse fraction that does not pass through the openings thereof. The coarse fraction forms the pretreated biomass, which typically has a higher fiber content as compared to the untreated hemicellulose rich biomass. As will be understood by those skilled in the art, the sieve is not limited to 0.85 mm openings and may include any other suitable sized openings based upon the biomass material and/or the amount of biomass to be retained as the coarse fraction.

In some embodiments, the pretreatment procedure also includes subjecting the coarse fraction and/or biomass to sonication, which increases breakdown of the coarse fraction and provides a material on which hydrolysis can more effectively and efficiently be performed. For example, following the screening procedure, sonication may include adding the coarse fraction to a liquid, such as water, and then sonicating the liquid/coarse fraction mixture with any suitable sonication device. Suitable sonication devices include any device capable of applying sound energy to the biomass and/or coarse fraction, such as, but not limited to, an ultrasonic homogenizer. After sonication and prior to hydrolysis, the coarse fraction and/or biomass is dewatered through any method for separating the coarse fraction from the water, such as, but not limited to, passing the liquid/coarse fraction through a mesh screen.

To produce a C5-rich hydrolyzate, in some embodiments, a mild dilute acid hydrolysis is performed on the hemicellulose rich biomass and/or the pretreated biomass. The mild dilute acid hydrolysis provides selective hydrolysis of the biomass and a cleaner C5-rich hydrolyzate with minimal degradation products. Any suitable device may be used for the dilute acid hydrolysis, including, but not limited to, a percolation reactor. For example, mild dilute acid hydrolysis of the biomass may be performed in a large volume percolation reactor with liquid recirculation, which permits an acid solution to be passed through a fibrous biomass material, then heated and recirculated through the reactor.

In this regard, in some embodiments of the presently-disclosed subject matter, to produce a sufficient hydrolyzate, an amount of solid biomass material is initially placed in a reactor and is then exposed to an acid solution that is percolated through the material at an elevated temperature and for a sufficient amount of time to allow the hydrolysis reaction occur. In some embodiments, the elevated temperatures used in accordance with the hydrolysis procedure range from about 100° C. to about 150° C. with a reaction time of about 30 to about 120 minutes. Of course, a number of acids can be used to effectuate a sufficient hydrolysis reaction including, in some embodiments, sulfuric acid, which may be included at a concentration of about 0.2% to about 0.4%. For further explanation and guidance relating to reaction conditions for producing a biomass hydrolyzate, see, e.g., Fonseca, et al., Biomass and Bioenergy, 21 (2014), 178-186, which is incorporated herein by reference in its entirety.

Typically, following the dilute acid hydrolysis, the hydrolyzate formed therein is neutralized and then the C5 sugars are isolated therefrom. Neutralizing the hydrolyzate includes adding a base, such as sodium hydroxide (NaOH), to the hydrolyzate. The base is added in any suitable amount for raising the pH of the hydrolyzate to a level sufficient for promoting boronate ester formation (e.g., neutral to basic pH). Suitable pH levels of the hydrolyzate include, but are not limited to, between 7.0 and 9.0, between 7.0 and 8.5, between 7.0 and 8.0, about 7.5, or any suitable combination, sub-combination, range, or sub-range thereof. For example, in some embodiments, neutralizing the hydrolyzate includes adding NaOH to a distillers dried grains (DDG) hydrolyzate in an amount sufficient to raise the pH of the hydrolyzate to 7.5. As will be appreciated by those skilled in the art, the amount of base added to the hydrolyzate will vary depending upon the starting pH and/or volume of the hydrolyzate, and the pH of the resulting hydrolyzate may be further adjusted with additional base or acid (i.e., hydrolyzate without any base added thereto) to raise or lower the pH, respectively.

After neutralizing the hydrolyzate, isolating the C5-sugar therefrom includes adding an excess amount of alkyl or aryl boronic acid (e.g., phenyl boronic acid (PBA)) to the hydrolyzate. Any suitable amount of PBA may be added to provide complexation with the C5-sugar. Suitable amounts of PBA include, but are not limited to, PBA:C5-sugar molar ratios of between 1 and 12, between 2 and 12, between 3 and 11, between 4 and 12, between 2 and 10, between 6 and 10, between 4 and 8, between 5 and 7, between 7 and 9, about 6, about 8, or any combination, sub-combination, range, or sub-range thereof. The resulting complexation, in turn, yields a furanose ester or diester (e.g., xylose diester or XDE), which may subsequently be cleanly extracted by using an organic solvent and separating the hydrolyzate mixture into an organic phase and an aqueous phase. For example, in some embodiments, isolating the C5-sugar from the hydrolyzate includes adding PBA to form a reaction mixture, stirring the reaction mixture, allowing the organic and aqueous phases to separate, and then isolating the organic layer. Other components that may be added to the hydrolyzate along with the PBA include, but are not limited to, toluene, methanol (MeOH), or a combination thereof.

The organic phase includes the ester or diester and the aqueous phase including the remainder of the hydrolyzate degradation products. In this regard, in some embodiments, the organic solvent can be derived from petroleum sources. In other embodiments, however, to avoid the use of crude-oil derived solvents to extract the esters or diesters formed by alkyl or aryl boronic acid complexation, the extraction of the esters or diesters is alternatively performed using natural solvents, such as plant derived triglycerides (e.g., vegetable oil, such as canola oil) as an organic solvent that can serve to eliminate the undesirable use of crude-oil derived solvents and other similar products in the generation of a C5 platform of biochemical and biofuels. Isolating the organic layer includes any suitable extraction method, such as, but not limited to, one or more extractions with toluene.

Following the extraction of the C5 sugar esters or diesters, in the next step of the process, the C5 sugar esters of diesters are precipitated from the organic phase by combining the organic phase with a boron capture agent, as illustrated in FIG. 1. It has been observed that the formation of a thermodynamically more stable boronic ester can drive the cleavage of boronic esters of six- and even certain five-membered ring 1,2-diols, such as are present in C5 sugar diesters (e.g., XDE). As such, the phrase, "boron capture agent" is used herein to refer to agents that are capable of driving the cleavage of such boronic esters. In some embodiments, the boron capture agent is selected from the group consisting of glycols or 1-2 or 1-3 amino diols or triols (e.g., norbornanediol (ND), ethylene glycol, and propylene glycol). In some embodiments, by making use of boron capture agents, the C5 sugars are precipitated and recovered in pyranose form that, in some embodiments, is then readily isolated by filtering the precipitate to obtain the C5 sugar in solid form. For example, isolating the C5-sugar may include adding propylene glycol (PG) to the organic phase including XDE, stirring the XDE/PG solution, then allowing the precipitated solids to settle, decanting the liquid portion of the organic phase, adding a solvent (e.g., diethyl ether) to the remaining humectant precipitate, stirring the precipitate and solvent, and collecting the resulting fine solids (e.g., D-xylopyranose) through filtration. The solid C5 sugar may then be used for conversion of the sugars to biochemical or biofuels, including, for example, chemical synthesis schemes that require the sugars to be in dry form.

Once the C5 sugar has been isolated, in some embodiments that make use of immobilized (such as polymer-supported) diols (e.g., ethylene glycol and propylene glycol) for precipitating the C5 sugars, the boronic acid is then recovered from the immobilized support by treating with an aqueous acid to cleave any formed boronic esters. Free boronic acid from the cleavage can then be removed into an organic phase, while the previously-utilized polymer diol is regenerated.

By making use of the above-described process, it is believed that the isolation of hemicellulose sugars (e.g., xylose or arabinose) from the dilute hydrolyzate stream in a dry form can effectively be used to yield a strong technical and economic impact in producing drop-in biofuels from biomass. In addition, the isolation process conducted under ambient conditions prevents further degradation of C5 sugars (due to high temperature) and maximizes the availability of the C5 sugars. The isolation process of xylose in dry form can also provide more process options other than fermentation to convert the sugars to a C5 platform of biochemical and biofuels and other bioproducts. For example, the production of jet fuels and their components from sustainable and renewable resources is paramount to the energy independence and security aspects of the United States. Utilizing renewable resources such as co-products from grain processing to produce jet fuels, i.e., "bio-jet fuels," is advantageous from the perspectives of the environment, process integration and economics, as well as energy independence and national security. These co-products are richer in hemicelluloses and the C5 sugars derived from these co-products can be converted via biochemical routes to higher-value bio-jet fuels and high energy density components of bio-jet fuels.

The presently-disclosed subject matter is further illustrated by the following specific but non-limiting examples. The following examples may include compilations of data that are representative of data gathered at various times during the course of development and experimentation related to the present invention. Additionally, some of the following examples may include prophetic statements, notwithstanding the numerical values, results and/or data referred to and contained in the examples.

EXAMPLES

It is appreciated that agriculture and agricultural processing are keys to economic development and employment in the United States. Indeed, the U.S. has several world-scale processing facilities to convert grain and other commercial crops to food products, sugars, alcohols and spirits, dietary fibers, industrial proteins, and the like. In connection with those facilities, agricultural processing generates significant amounts of biomass, such as soy hulls from soybean processing, rice hulls from rice milling, corn fiber from wet milling or dry milling, bagasse from sugarcane processing, pulp from sugar beets processing, and other forms of biomass. Those amounts are captive sources of biomass that significantly minimize or eliminate the transportation, storage, and other logistics costs that have to date been hurdles to the utilization of biomass for the production of a C5 platform of biochemical and biofuels. In addition to low-cost availability, however, the above-mentioned feedstocks are also important in that either they are mechanically processed and/or have a composition of higher hemicellulose, compared to cellulose, and lower lignin (see, e.g., Table 1, showing the composition of fibers from some example feedstocks). This, in turn, means that high temperature and pressure are not needed to process those fibers for C5 sugar extraction.

The high hemicellulose containing biomass varieties mentioned in Table 1 are from agricultural processing plants and are available in large volumes, as shown in Table 2. These biomass varieties are available across the regions of the United States and can be used to produce C5 sugars.

TABLE 1

Comparison of fiber composition from high hemicellulose containing CAPTIVE agricultural biomasses and wood.

| Composition (%) | Corn fiber from kernels | Soy hulls from soybeans | Rice Hulls | Oat hulls | Bagasse from sugarcane | | Pulp from sugar beets processing | Wood | |
| --- | --- | --- | --- | --- | --- | --- | --- | --- | --- |
| | | | | | Fiber bundle fraction | Pith fraction | | Soft | Hard |
| hemicellulose | 39-40 | 15-20 | 33.7 | 48.3 | 29 | 32 | 32 | 25-29 | 25-35 |
| cellulose | 11-13 | 29-51 | 47.5 | 38.8 | 45 | 39 | 21 | 40-44 | 43-47 |
| lignin | 3-6 | 1-4 | 18.6 | 11.6 | 18 | 16 | 2.4 | 25-31 | 16-24 |

TABLE 2

Availability of high hemicellulose containing agricultural biomass varieties.

| Biomass Type | Sources | US Region | MM tons/year | Comments |
|---|---|---|---|---|
| Corn fiber from kernels | Wet and dry milling plants | Midwest | 24 | 12 billion bushels of corn |
| Corn cobs from grain harvesting | Corn fields and storage silos | Midwest | 58 | Cob to grain ratio of 1:5.6 Not a captive biomass |
| Soy hulls from soybeans | Soybean oil crushing plants | Midwest | 8 | 3.1 billion bushels of soybeans per year |
| Rice hulls | Rice mills | South | 2 | 213 MM cwt per year |
| Rice bran | Rice mills | South | 1.2 | |
| Oat hulls | Cereal oat plants | Midwest | 6 | 66 MM bushels per year |
| Wheat bran | Wheat milling | North, Northwest, Midwest, South | 9 | 2,130 MM bushels per year |
| Bagasse from sugarcane processing | Cane sugar plants | South | 10 | 26.7 MM tons of sugarcane processed |
| Beet pulp from sugar beet processing | Beet sugar plants | Northwest and Upper Midwest | 2 | 28.8 MM tons of sugar beets processed |

Figure 2:
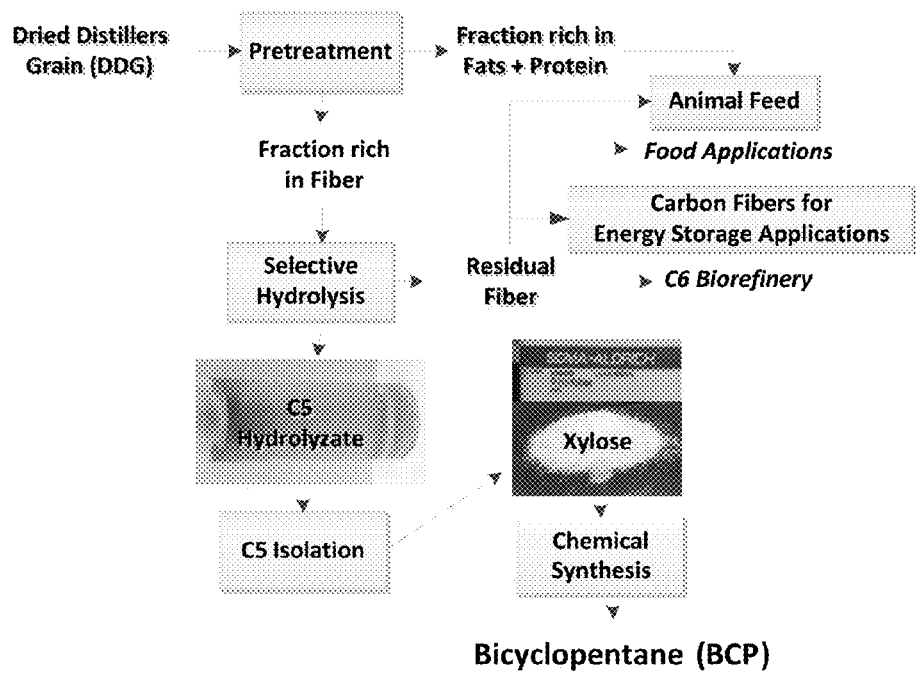
FIG. 2 is a schematic view of a bio-refinery concept for high hemicellulose containing lignocellulosic biomass.
Figure 3:
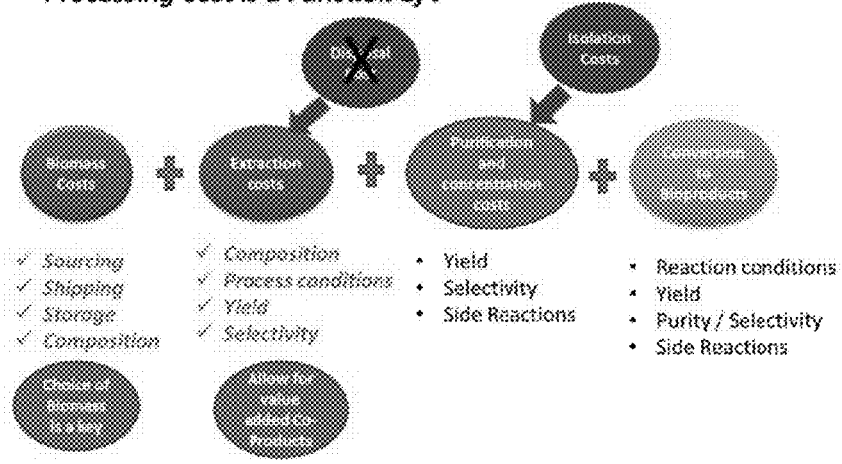
FIG. 3 is a schematic view of the processing cost for biofuels using hemicellulose rich agricultural biomass.

Based on composition, obtainable varieties, and availability across multiple geographic regions of the US, it was thus believed that the captive hemicellulose-rich agricultural biomass varieties mentioned above could be of use in reducing the overall processing cost of producing biofuels and bioproducts (see, e.g., FIG. 3 below). In this regard, a C5-biorefinery process was developed that made use of individual process steps using corn (kernel/hull) fiber using dried distillers grain (DDG) as "captive" biomass, as shown schematically in FIG. 2. The process steps included the production of a C5-rich hydrolyzate using selective hydrolysis and the isolation of D-xylose from the hydrolyzate. Without wishing to be bound by any particular theory or mechanism, it was believed that the C5 isolation process would have a high impact on the overall process due to its potential to reduce the number of high energy consuming concentration and purification steps.

Example 1—Production of C5-Rich Hydrolyzate

As a first step in the C5-isolation/biorefinery process, a biomass hydrolyzate was produced, which preferably was a C5-rich hydrolyzate with high concentration of C5 sugars and a low concentration of associated degradation products and C6 sugars. As discussed above, the choice of hemicellulose rich biomass and a hydrolysis process selective to C5 sugars was believed to deliver a desired C5-rich hydrolyzate that could then effectively and efficiently be used for the isolation of C5 sugars. Briefly, the C5-rich hydrolyzate was produced using a 2-stage hydrolysis process described previously and developed at the Conn Center at the University of Louisville (see, e.g., D. A. Fonseca, R. Lupitsky, D. Timmons, M. Gupta, J. Satyavolu. Towards Integrated Biorefinery from Dried Distillers Grains: Selective Extraction of Pentoses using Dilute Acid Hydrolysis. Biomass and Bioenergy. 71: 178-186 (2014), which is incorporated herein by reference in its entirety). The reaction conditions for the hydrolysis process were optimized to provide higher selectivity to C5 sugars (D-xylose), a low concentration of C6 sugars, and a low level of degradation products (furfural). The 2-stage hydrolysis also reduced the level of arabinose in the hydrolyzate.

TABLE 3

Xylose enrichment using a 2-stage hydrolysis[a]

| Compound | First stage[b] (mg/mL) | Second stage[c] (mg/mL) |
|---|---|---|
| Arabinose | 5.41 | 2.52 |
| Xylose | 1.23 | 14.46 |
| Glucose | 0.26 | 2.22 |
| Glycerol | 1.16 | 0.88 |
| Acetic acid | 0.53 | 1.84 |
| 5-HMF | 0.01 | 0.16 |
| Furfural | 0.02 | 1.07 |

[a]DDG pretreatment: screening;
[b]110° C. and 0.2 wt. % $H_2SO_4$;
[c]140° C. and 0.4 wt. % $H_2SO_4$ The main component of the hydrolyzate was D-xylose (Table 3), with only small amounts of other sugars, such as arabinose, glucose, mannose, and galactose. The hydrolyzate also contained several minor byproducts, such as various furans (furfurals, 5-hydroxymethyl-furfural (5-HMF)), phenolics, weak acids (acetic acid, levulinic acid, formic acid, etc.), oligosaccharides and some raw material extractives (tannic and terpene acids). To overcome the challenges associated with separation of such a complex mixture and to obtain a pure starting monosaccharide, a precipitation protocol was then developed that delivers D-xylose in pyranose form as required for its subsequent synthetic transformations.

Example 2—Isolation of Xylose from Hydrolyzate

Figure 4:
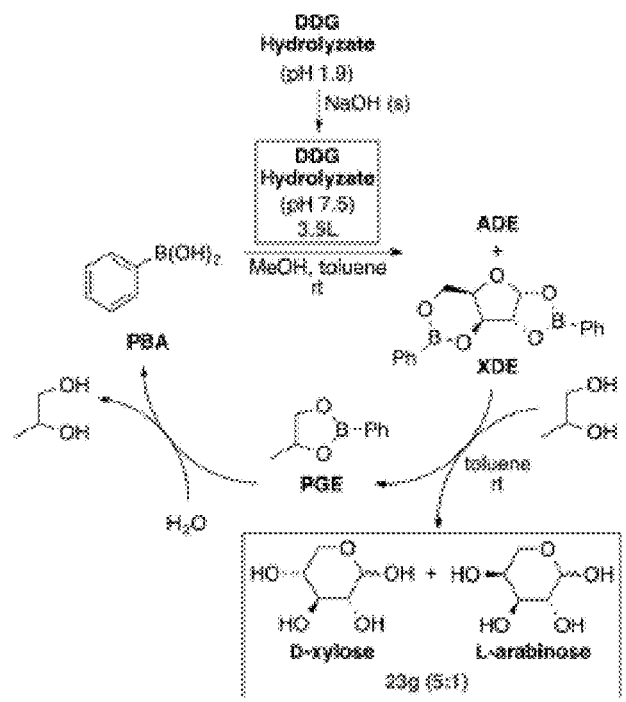
FIG. 4 is a schematic view of a pentose isolation and PBA recovery cycle; DDG=distillers dried grains; ADE=boronic diester of arabinose; XDE=xylose di-ester $(PhB)_2(D\text{-}XylfH_{-4})$, PG=propylene glycol, PGE=propylene glycol boronic ester, PBA=phenylboronic acid.

After preparation of the C5 rich hydrolyzate, the isolation of xylose (i.e., a C5 sugar) was carried out using a three step process. The first step in the process involved phenylboronic acid (PBA) complexation of xylose to form the furanose diester XDE, see, e.g., Reichvilser, M. M.; Heinzl, C.; Klufers, P., Boronic acid mono- and diesters of the aldopentoses. Carbohydrate Research 2010, 345, (4), 498-502, which is also incorporated herein by reference in its entirety. Briefly, the xylose isolation process was developed using hydrolyzate containing D-xylose as the principal C5 sugar (ca. 15 mg/mL D-xylose by HPLC) among several other components (see Table 3). As illustrated in FIG. 4, to begin isolating the D-xylose, the hydrolyzate was first neutralized (NaOH) prior to addition of excess PBA, the amount of which was determined from prior HPLC measurement of xylose concentration in the hydrolyzate where a stoichiometry study on equivalents of PBA needed for optimal complexation and isolation of xylose revealed that 4 equivalents PBA/xylose afforded high levels of xylose extraction for hydrolyzate at pH 7.8. HPLC analysis of the extracted hydrolyzate indicated that approximately 90% of the xylose was consumed using those conditions. NMR and HPLC analyses of the extract further showed that, in addition to unreacted $PhB(OH)_2$ and the product XDE, the boronic diester of arabinose (ADE) was also extracted in minor quantities (XDE:ADE, 9:1). No other C5 sugar-boronic ester or diester adducts were observed in the toluene extract. In this regard, and without wishing to be bound by any particular theory or mechanism, it was believed that reducing the number of PBA equivalents required in this step for even more efficient extraction of xylose would likely depend on hydrolyzate treatment efforts (e.g., improved separation of sugars from sugar degradation products) as hydrolyzate that was further enriched in xylose would be expected to require less PBA. Indeed, the quality of hydrolyzate was expected to have an important impact on PBA: xylose stoichiometry. Further details for treating the hydrolyzate to achieve a more suitable starting pH and improved composition were developed. In short, however, a higher hydrolyzate pH at the onset of the first step would require less NaOH for neutralization purposes, and that, in turn, would lead to volume and solubility issues. Since PBA added to hydrolyzate coordinates to and/or covalently bonds most solutes (e.g., C5 sugars, sugar degradation products, fibers, etc.), a hydrolyzate further enriched in xylose would thus require less PBA equivalents for effective xylose complexation.

Subsequent to PBA complexation of xylose to form XDE, XDE was then cleanly extracted from the mixture using toluene, while unreacted PBA and minor amounts of the boronic diester of arabinose $(PhB)_2(D\text{-}ArapH_{-4})$ were also extracted into the toluene phase. During this process, it was observed that XDE precipitates from the hydrolyzate as PBA was added in the absence of organic solvent. Initial studies determined that toluene extraction was preferable for isolation of XDE in comparison to XDE precipitate filtration due to interfering hydrolyzate fibers; however, given complications in subsequent reagent recovery operations as well as economic considerations, isolation of XDE using a precipitation protocol can be an alternative. Hydrolyzate filtration prior to PBA addition can also be a route to remove particulates. Volume and temperature variables also were expected to be key variables for optimizing a precipitation protocol. Finally, additives (e.g., NaCl, other salts) can also be potentially used to enhance the precipitation of XDE directly from the hydrolyzate-PBA reaction.

After the isolation of XDE, the next step in the isolation process makes use of a previously-described observation that formation of a thermodynamically more stable boronic ester can drive the cleavage of boronic esters of six- and even certain five-membered ring 1,2-diols, such as are present in XDE. As such, initially the toluene phase containing XDE was directly treated with cis-exo-2,3-norbornanediol (ND) at room temperature to effect transesterification and form, in near quantitative yield, the corresponding phenyl boronic ester of ND and resulted in the precipitation of xylose in its pyranose form. The isolated yield of monosaccharides was nearly quantitative. NMR analysis of the isolated solids indicated, in close agreement with the XDE:ADE ratio, an approximately 9:1 mixture of xylose and arabinose. The ratio varied depending on the composition of these sugars in the starting hydrolyzate. Importantly, the presence of arabinose did not adversely affect use of the isolated material in the biofuel synthesis route since both xylose and arabinose could be used as starting material. However, the newly formed boronic ester proved too stable to perform subsequent PBA recovery operations, so a screen for other 1,2-diols was conducted.

Figure 5:
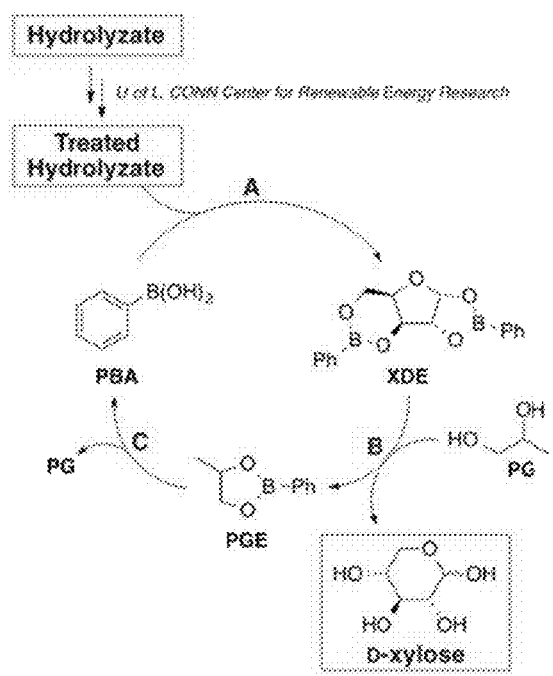
FIG. 5 is a schematic view of a xylose isolation process showing a three-step cycle used to isolate D-xylose from hydrolyzate; XDE=xylose di-ester $(PhB)_2(D\text{-}XylfH_{-4})$, PG=propylene glycol, PGE=propylene glycol boronic ester, PBA=phenylboronic acid.

The screen of readily available, more cost effective 1,2-diols revealed that ethylene glycol and propylene glycol (PG) also resulted in precipitation of xylose from the toluene extract (FIG. 5). In both cases, xylose isolation was near quantitative. When using PG as the XDE decomplexation agent, an excess of PG was required to achieve near 100% liberation of xylose, and an optimal PG to XDE stoichiometry was established at 5 PG/XDE. The phenyl boronic ester of proplylene glycol (PGE, FIG. 6) also remained in solution and was capable of being processed in the next step for recovery of PBA.

In this portion of the xylose isolation process, the xylose precipitates as D-xylopyranose (ca. 1:2 mixture of α:β anomers). The crystalline precipitate was readily harvested by filtration. The filtrate contained PGE, the corresponding boronic ester of PG. The dry xylose obtained in this manner was also accompanied by minor quantities of D-arabinose. That xylose and arabinose mixture was again suitable for direct use in the first step of a process for conversion to bio-derived jet fuel. In all organic solvents examined, xylose precipitated from solution in its pyranose form, although with differing anomeric ratios.

In an effort to develop an entirely biorenewable approach, XDE decomplexation in a non-crude oil-derived solvent was also examined. Namely, solid XDE was dissolved in refined vegetable oil (pure canola oil, Crisco™). Addition of PG (5 equivalents/XDE) resulted in clean precipitation of D-xylose as confirmed by NMR characterization. The availability from natural sources, ease of handling (non-toxic, non-volatile), cost (less than 400/pound), and recycling options after use (used cooking oil for energy market) made vegetable oil an ideal choice for dissolution of the XDE precipitate isolated from PBA reaction with hydrolyzate.

Figure 7:
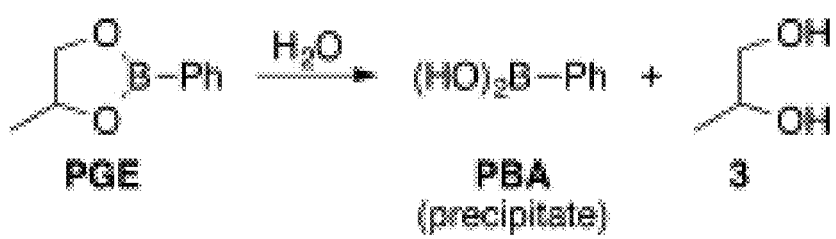
FIG. 7 is a process view of the hydrolysis of PGE to recover PGA.

Subsequent to recovery of the xylose, a step was developed for PBA recovery for subsequent runs of the cycle. Briefly, in this step, the toluene solution of PGE was vigorously mixed with dilute aq. HCl to effect hydrolysis of the boronic ester moiety. PBA was then isolated on evaporation and recycling of the toluene phase whereas PG was extracted into the aqueous acid phase for subsequent separation using membrane technology. Alternatively, in some embodiments, as illustrated in FIG. 7, the step of recovering PBA may use $H_2O$ in place of aq. HCl.

With respect to the PBA recovery step, others have reported conditions for efficient dilute acid hydrolysis of PG-derived boronic esters. However, during initial studies, efforts to hydrolyze PGE for recovery of PBA were not as successful. Reaction of the PGE toluene solution after removal of precipitated xylose (i.e., Step B filtrate) with an equivalent volume 0.1 N HCl overnight at room temperature gave approximately 50% hydrolysis. The use of stronger acid conditions, or application of heat or even longer reaction times, however, did not improve the extent of PBA formation. Consequently, PBA was recovered on toluene removal as an approximately 1:1 mixture with PGE. Presumably, rapid re-formation of PGE in the organic phase competes with hydrolysis. Indeed, other have previously noted this problem and used water soluble tridentate ligands, such as tris(hydroxymethyl)methane derivatives, to chelate boron for clean isolation of the diol component. Yet, since the focus of the present studies were principally in recovering PBA, that prior strategy could not be readily applied.

The present efforts to hydrolyze PGE, either neat followed by organic extraction of PBA or using solvents other than toluene, all generally afforded 30-50% PBA contaminated with PGE. Similar results were noted for hydrolysis of EGE, the boronic ester obtained from XDE boron-decomplexation using ethylene glycol. As such, and again without wishing to be bound by any particular theory or belief, it was believed that the use of a solid-supported boron capture strategy was preferable for separation of PBA from diol after hydrolysis.

Example 3—Evaluation of Alternative Processing Conditions

Figure 6:
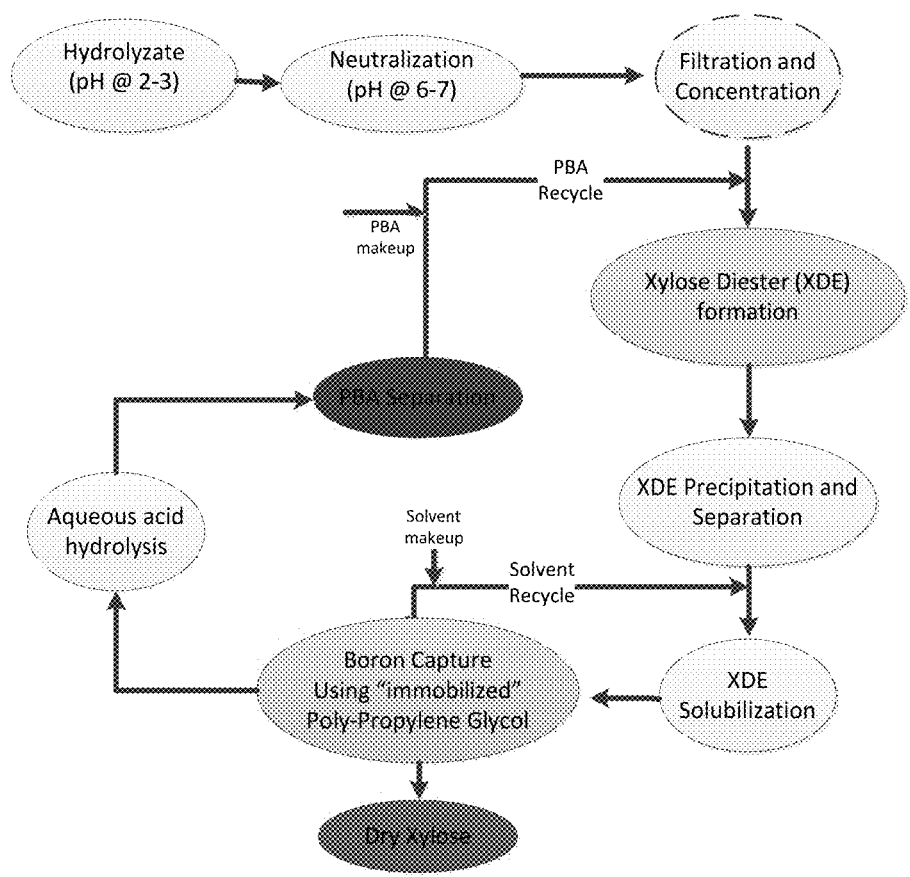
FIG. 6 is a schematic view of a process for isolating xylose from "C5 rich" hydrolyzate.

FIG. 6 below is a process schematic for the xylose isolation process from hydrolyzate that was initially developed and that is described above in Examples 1-2. As mentioned, this process was conducted under ambient conditions and delivered xylose in dry form for subsequent conversion to a biofuel using chemical synthesis process steps. Table 4, however, provides a summary of technical challenges and needs that are based on that process and solutions or alternatives that may be utilized in connection with the process. Based on those identified alternative, additional technical tasks were identified to further the develop and/or identify alternative processing conditions.

The first task identified related to providing the hydrolyzate at a suitable pH (use of dicarboxylic acids). The selective hydrolysis that was done to produce the hydrolyzate used dilute sulfuric acid and the hydrolyzate pH was typically between 2 and 3. Even though the hydrolyzate included a high level of xylose and low levels of degradation products (see Table 3), the resulting pH still required high levels of NaOH to bring the pH to 6-7. An observation of the complexation of xylose using PBA, however, was that it was effective between a solution pH of 6-7. In this regard, and as previously reported, dicarboxylic acids such as maleic and oxalic acids have been suggested as alternatives for sulfuric acid for the extraction of C5 sugars, even though they more expensive on a weight basis. Maleic and oxalic acids have higher pKa values than sulfuric acid and thus a higher solution pH, compared to mineral acids such as sulfuric acid.

The second task identified related to providing the hydrolyzate at a suitable xylose concentration. As mentioned in Table 4, it was possible to reduce the equivalents of PBA during complexation by increasing the concentration of xylose. As is, the dry solids (% DS) of the hydrolyzate were less than 10%. As such, optimizing the incoming pH of the hydrolyzate as well as % DS was believed to have a positive impact on the cost of neutralization as well the quality of the hydrolyzate used for XDE formation. As reported previously, since xylose was stable in boiling aqueous oxalic acid, it was advantageous to use the hydrolyzate again. This would reduce the cost of acid as well as increase the concentration of xylose. It was also possible to concentrate the hydrolyzate by evaporation and crystallize oxalic acid, which can increase the concentration of xylose in solution as well as raise its pH.

TABLE 4

Summary of research and proposed alternative to xylose isolation process depicted in FIG. 6.

| Step A | |
|---|---|
| Current | 4 equiv. PBA/xylose added to neutralized hydrolyzate to form XDE; XDE and unreacted PBA then extracted into toluene |
| Challenges | Moderate: Cost associated with hydrolyzate neutralization (NaOH); excess PBA, also uneconomical, requires more PG be used in next step; this process uses toluene, which is produced from crude oil |
| Alternative | reduce equivalents of PBA required for XDE formation by increasing xylose concentration in the hydrolyzate using methods that also deliver hydrolyzate having higher pH (to decrease subsequent NaOH consumption); develop optimal XDE precipitation protocol that avoids the use of organic solvent |
| Step B | |
| Current | excess PG added to XDE toluene solution to effect xylose precipitation; xylose harvested by filtration (>90% of theoretical isolated) |
| Challenges | Minor: expense associated with using and recycling toluene; cost associated with using excess PG |
| Alternative | immobilize boron-capture motif (e.g., 1,2-diol, such as PG) on solid support/polymer; determine optimal structural and loading requirements of polymer for efficient XDE boron-decomplexation to precipitate xylose; develop protocol that uses refined veg. oil as medium for precipitating xylose on introduction of polymer |
| Step C | |
| Current | toluene solution of PGE is reacted with dil. aq. acid; PBA recovered (as a mixture with PGE) on evaporation/recycling of toluene; PG recovery requires aq. phase neutralization (NaOH) followed by PG separation - one option is separation of PG using NF membranes. |
| Challenges | Major: PBA recovery low (~50% of theoretical isolated), subsequent PBA purification required; expense high for recovery of PG (NaOH neutralization, membrane procedure); toluene distillation step required |
| Alternative | develop acid hydrolysis-polymer regeneration protocol to liberate bound PBA from polymer (PBA precipitation, recovery by filtration) and to optimize re-use of the polymer for subsequent XDE decomplexation cycles in recycled oil |

The third task identified related to selecting the solvent for XDE solubilization. In the present studies, it was observed that XDE was insoluble in water and could be precipitated from hydrolyzate solution. A solvent was then used to solubilize the XDE in order to facilitate the isolation of xylose and recovery of PBA. After dissolving the XDE, a boron capture agent was added to the solvent phase. As PBA attached to the capture agent (transesterification), the xylose then precipitated out of the solvent phase. The recovery of xylose, PBA and the solvent, however, depended on the type of solvent being used, although the above-described work using toluene and refined canola oil was efficient.

The fourth task identified related to immobilizing the boron capture agent. This approach to isolate xylose and recover PBA was to affix a boron capture agent on an immobilized phase. During preliminary tests, norbornene diol and propylene glycol were evaluated—both proved effective at capturing PBA and releasing xylose in a solvent phase. However, when a dilute aqueous acid was used to recover PBA, propylene glycol released PBA better than the norbornene diol. As such, it was proposed to use propylene glycol functionality, or a similar structural motif as determined by experiment, for boron capture by immobilization on a polymer surface (preferably a membrane flat sheet or hollow fiber configuration). Efficient transesterification of XDE with concomitant release of xylose is a primary technical focus of this task.

Figure 8:
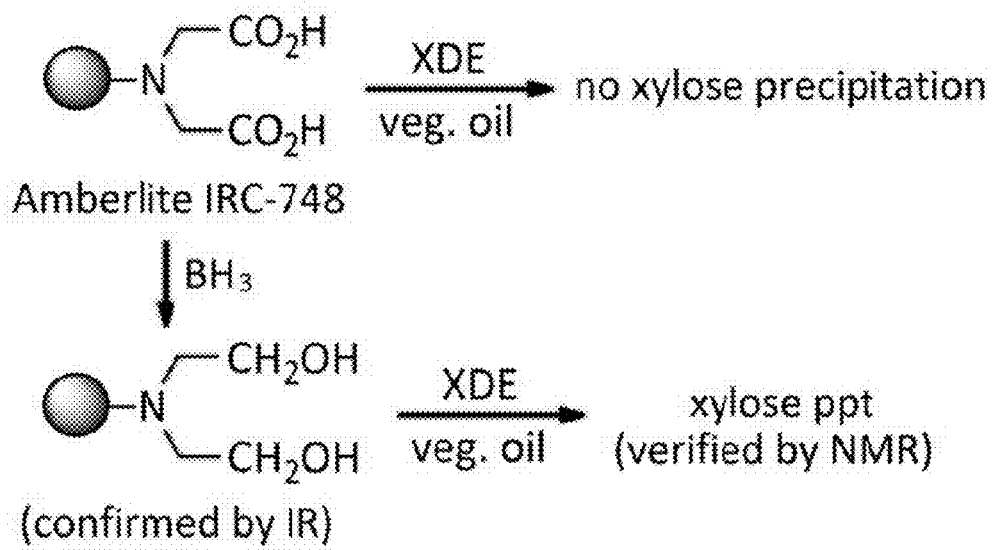
FIG. 8 is a schematic view of a preliminary polymer-supported XDE boron-decomplexation result.

The fifth task identified related to using solid-supported boron capture. The application of solid-supported chelating agents for boron sequestration has been previously described, particularly in desalination operations using functionalized reverse osmosis membranes. Indeed, literature on structural motifs used to complex boron has led to several applications in which boron is retained by a functionalized polymer or membrane matrix. In an effort to explore whether that approach could be used to effect XDE decomplexation, the commercial resin amberlite IRC-748 (FIG. 8) was reacted with XDE dissolved in vegetable oil (to mimic the action of PG). No free xylose resulted from that attempt. However, reaction of XDE with the diol-substituted resin derived on reduction of the amberlite beads using borane (FIG. 8) resulted in xylose precipitation, albeit in modest yield. Those promising preliminary result confirmed that a solid-supported strategy could be developed for transesterification of boronic esters—PBA can be retained on a polymer or membrane matrix given appropriate functionality. Consequently, the next step is to investigate the reaction of XDE in oil with a variety of solid-supported boron chelating functionalities, particularly configurations of 1,2-diols. Since the specific tasks of (a) efficient XDE boron decomplexation by polymer-bound functionality and subsequent (b) efficient hydrolytic release of the polymer-bound PBA have not been previously investigated, factors leading to clean conversion of XDE to xylose with efficient recovery of PBA are determined. Once established, those factors can be engineered to serve as an integral component of fibers, filaments, or even membranes (e.g., polysulfone) that can be introduced into the XDE oil solution to cause xylose precipitation in bulk and then be removed for PBA recovery.

Figure 9:
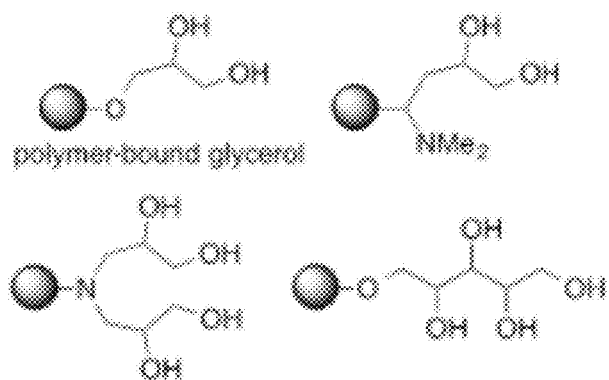
FIG. 9 is a structural view of various polymer supported glycol motifs.

One of the goals for this task includes screens of commercial resins, such as polymer-bound glycerol, polymer-bound 2-hydroxymethyl-1,3-propanediol (both from Sigma-Aldrich) and polymer-bound N-methyl-D-glucamine. Modest synthetic investigations are also conducted on functionalized polymers to generate structural motifs deemed well-suited for boron chelation, such as those depicted in FIG. 9. Furthermore, several straightforward methods for preparation of functionalized macroporous polymers have been reported and will be explored as needed. It is thought that the polymer can be introduced (e.g., submersed in XDE oil solution) to effect xylose precipitation, then removed and replaced by new polymer until all XDE has been decomplexed. The PBA-loaded polymers can then be subjected to regeneration conditions using dilute acid-mediated hydrolysis of the bound boronic ester. The key feature here is that liberated PBA precipitates in the aqueous medium (FIG. 10) and cannot be readily recaptured, unlike our previous attempts at biphasic extraction of liberated PBA.

Summary of Examples 1-3

Figure 10:
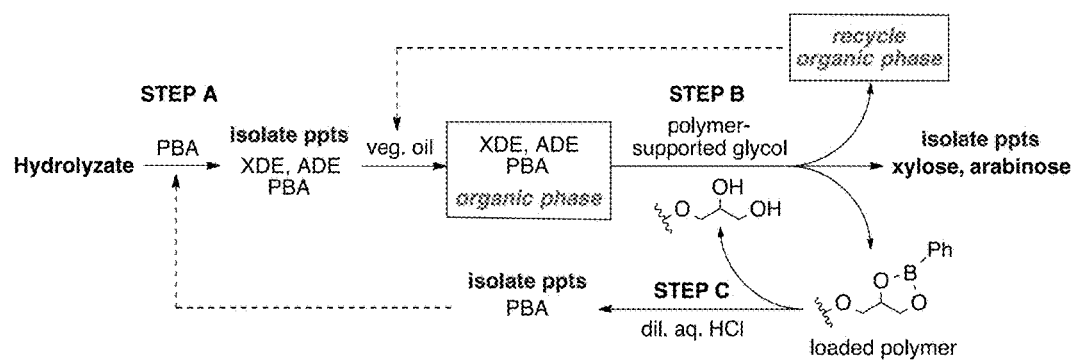
FIG. 10 is a schematic view of a xylose isolation approach using polymer-supported reagent.

The features of the above-described 3-step isolation process are summarized in FIG. 10. Notably, (a) the target sugar xylose is readily isolated in solid form by simple filtration; (b) key reagent phenyl boronic acid is recovered from a functionalized polymer or membrane using an aqueous acid regeneration protocol; and (c) a single non-crude oil-derived organic phase is used and recycled throughout the process.

Throughout this document, various references are mentioned. All such references are incorporated herein by reference, including the references set forth in the following list:

REFERENCES

1. Yang, J. F.; Li, N.; Li, G. Y.; Wang, W. T.; Wang, A. Q.; Wang, X. D.; Cong, Y.; Zhang, T., Synthesis of renewable high-density fuels using cyclopentanone derived from lignocellulose. Chemical Communications 2014, 50, (20), 2572-2574.
2. Yang, Y. L.; Du, Z. T.; Huang, Y. Z.; Lu, F.; Wang, F.; Gao, J.; Xu, J., Conversion of furfural into cyclopentanone over Ni—Cu bimetallic catalysts. Green Chemistry 2013, 15, (7), 1932-1940.
3. Grohmann, K.; Torget, R.; Himmel, M., Optimization of dilute acid pretreatment of biomass. Seventh Symp. Biotechnol. Fuels Chem. 1985, 15, 59-80.
4. Lloyd, T. A.; Wyman, C. E., Combined sugar yields for dilute sulfuric acid pretreatment of corn stover followed by enzymatic hydrolysis of the remaining solids. Bioresource Technology 2005, 96, (18), 1967-1977.
5. Torget, R.; Himmel, M. E.; Grohmann, K., Dilute Sulfuric-Acid Pretreatment of Hardwood Bark. Bioresource Technology 1991, 35, (3), 239-246.
6. Pan, X. J.; Arato, C.; Gilkes, N.; Gregg, D.; Mabee, W.; Pye, K.; Xiao, Z. Z.; Zhang, X.; Saddler, J., Biorefining of softwoods using ethanol organosolv pulping: Preliminary evaluation of process streams for manufacture of fuel-grade ethanol and co-products. Biotechnology and Bioengineering 2005, 90, (4), 473-481.
7. Ferraz, A.; Rodriguez, J.; Free, J.; Baeza, J., Biodegradation of Pinus radiate softwood by white- and brown-rot fungi. World J. Microbiol. Biotechnol. 2001, 17, 31-34.
8. Lee, J. W.; Jeffries, T. W., Efficiencies of acid catalysts in the hydrolysis of lignocellulosic biomass over a range of combined severity factors. Bioresource Technology 2011, 102, (10), 5884-5890.
9. Fonseca, D. A.; Lupitskyy, R.; Timmons, D.; Gupta, M.; Satyavolu, J., Towards Integrated Biorefinery from Dried Distillers Grains: Selective Extraction of Pentoses using Dilute Acid Hydrolysis. Accepted for publication in Biomass and Bioenergy 2014.
10. Lupitsky, R.; Staff, C.; Satyavolu, J., Towards Integrated Refinery from Dried Distillers Grains: Evaluation of Feed Application for Co-products. Accepted for publication in Biomass and Bioenergy 2014.
11. Werpy, T.; Petersen, G. Top Value Added Chemicals from Biomass: Results of screening for potential candidates from sugars and synthesis gas; Volume 1; Report DOE/GO-102004-1992 U.S. Department of Energy, Office of Energy Efficiency and Renewable Energy. www.nrel.gov/docs/fy04osti/35523.pdf: 2004.

12. Rafiqul, I. S. M.; Sakinah, A. M. M., Design of process parameters for the production of xylose from wood sawdust. Chemical Engineering Research & Design 2012, 90, (9), 1307-1312.
13. Tortosa, C. I. G.; Breijo, F. J. G.; Yufera, E. P., An Economic-Process for Preparation of Xylose and Derivatives by Hydrolysis of Corn Cobs. Biological Wastes 1990, 33, (4), 275-286.
14. Herrera, A.; Tellez-Luis, S. J.; Ramirez, J. A.; Vazquez, M., Production of xylose from sorghum straw using hydrochloric acid. Journal of Cereal Science 2003, 37, (3), 267-274.
15. Chandel, A. K.; da Silva, S. S.; Singh, O. V. Detoxification of Lignocellulosic Hydrolysates for Improved Bioethanol Production. http://cdn.intechopen.com/pdfs-wm/20063.pdf; 2011.
16. Reichvilser, M. M.; Heinzl, C.; Klufers, P., Boronic acid mono- and diesters of the aldopentoses. Carbohydrate Research 2010, 345, (4), 498-502.
17. Roy, C. D.; Brown, H. C., A comparative study of the relative stability of representative chiral and achiral boronic esters employing transesterification. Monatshefte Fur Chemie 2007, 138, (9), 879-887.
18. Roy, C. D.; Brown, H. C., Stability of boronic esters—Structural effects on the relative rates of transesterification of 2-(phenyl)-1,3,2-dioxaborolane. Journal of Organometallic Chemistry 2007, 692, (4), 784-790.
19. US EPA Storm Water Technology Factsheet, United States Environmental Protection Agency, Office of Water, Washington, D.C., EPA 832-F-99-04. September 1999.
20. Kaupp, G.; Naimi-Jamal, M. R.; Stepanenko, V., Waste-free and facile solid-state protection of diamines, anthranilic acid, diols, and polyols with phenylboronic acid. Chemistry—a European Journal 2003, 9, (17), 4156-4160.
21. Sun, J.; Perfetti, M. T.; Santos, W. L., A Method for the Deprotection of Alkylpinacolyl Boronate Esters. Journal of Organic Chemistry 2011, 76, (9), 3571-3575.
22. Matteson, D. S.; Man, H. W., Hydrolysis of substituted 1,3,2-dioxaborolanes and an asymmetric synthesis of a differentially protected syn,syn-3-methyl-2,4-hexanediol. Journal of Organic Chemistry 1996, 61, (17), 6047-6051.
23. Starrkirclr, K. S.; Reinach, H. L. Process for the production of xylose, U.S. Pat. No. 3,586,537. 1971.
24. Kabay, N.; Guler, E.; Bryjak, M., Boron in seawater and methods for its separation—A review. Desalination 2010, 261, (3), 212-217.
25. Bull, S. D.; Davidson, M. G.; Van den Elsen, J. M. H.; Fossey, J. S.; Jenkins, A. T. A.; Jiang, Y. B.; Kubo, Y.; Marken, F.; Sakurai, K.; Zhao, J. Z.; James, T. D., Exploiting the Reversible Covalent Bonding of Boronic Acids: Recognition, Sensing, and Assembly. Accounts of Chemical Research 2013, 46, (2), 312-326.
26. Carboni, B.; Pourbaix, C.; Carreaux, F.; Deleuze, H.; Maillard, B., Boronic ester as a linker system for solid phase synthesis. Tetrahedron Letters 1999, 40, (45), 7979-7983.
27. Leznoff, C. C.; Wong, J. Y., The Use of Polymer Supports in Organic Synthesis. III. Selective Chemical Reactions on One Aldehyde Group of Symmetrical Dialdehydes. Canadian Journal of Chemistry 1973, 51, (22), 3756-3764.
28. Fu, X. A.; Li, M.; Knipp, M. H.; Nantz, M. H.; Boursamra, M., Noninvasive Detection of Lung Cancer Using Exhaled Breath. Cancer Medicine 2014, 3, 174-181.
29. Knipp, R. J.; Li, M.; Fu, X.-A.; Nantz, M. H., A Versatile Probe for Chemoselective Capture and Analysis of Volatile Carbonyl Compounds from Exhaled Breath. Submitted to Analytical Chemistry.
30. Alonso, D. M.; Bond, J. Q.; Dumesic, J. A., Catalytic conversion of biomass to biofuels. Green Chemistry 2010, 12, (9), 1493-1513.
31. Huber, G. W.; Iborra, S.; Corma, A., Synthesis of transportation fuels from biomass: Chemistry, catalysts, and engineering. Chemical Reviews 2006, 106, (9), 4044-4098.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A process for isolating a C5 sugar from a biomass hydrolyzate, comprising:
providing a biomass hydrolyzate including a C5 sugar;
forming a neutral boronic ester or diester of the C5 sugar by adding an amount of alkyl or aryl boronic acid to the biomass hydrolyzate at a pH consisting of about 7 to about 9 to complex the C5 sugar with the alkyl or aryl boronic acid;
extracting the neutral boronic ester or diester of the C5 sugar from the biomass hydrolyzate into an organic solvent to obtain an organic phase;
precipitating the C5 sugar from the organic phase using a boron capture agent; and
isolating the C5 sugar from the precipitate.

2. The process of claim 1, further comprising the step of recovering an amount of boronic acid subsequent to isolating the C5 sugar.

3. The process of claim 2, wherein the boronic acid is boronic acid anhydride.

4. The process of claim 2, wherein the step of recovering the boronic acid comprises aqueous acid hydrolysis of the boron capture agent.

5. The process of claim 1, wherein the C5 sugar is xylose or arabinose.

6. The process of claim 1, wherein the step of providing a biomass hydrolyzate comprises subjecting a biomass to a dilute acid hydrolysis in a reactor.

7. The process of claim 6, further comprising the step of pretreating the biomass to obtain an enriched fiber fraction of biomass prior to subjecting the biomass to the dilute acid hydrolysis.

8. The process of claim 7, wherein the step of pretreating the biomass comprises screening the biomass to obtain a coarse biomass fraction and sonicating the coarse biomass fraction.

9. The process of claim 1, wherein the biomass hydrolyzate is produced using a hemicellulose-rich agricultural biomass.

10. The process of claim 9, wherein the hemicellulose-rich agricultural biomass is comprised of materials selected from the group consisting of soy hulls obtained from soybean processing, rice hulls obtained from rice milling, corn fiber obtained from wet milling or dry milling, bagasse from sugarcane processing, pulp from sugar beet processing, distillers grains, and combinations thereof.

11. The process of claim 1, wherein the alkyl or aryl boronic acid comprises phenyl boronic acid.

12. The process of claim 1, wherein the organic solvent is synthetic and is derived from petroleum sources.

13. The process of claim 1, wherein the organic solvent is derived from natural sources.

14. The process of claim 13, wherein the organic solvent comprises plant-derived triglycerides.

15. The process of claim 14, wherein the organic solvent is vegetable oil.

16. The process of claim 1, wherein the boron capture agent is immobilized.

17. The process of claim 1, wherein the boron-capture agent is a glycol.

18. The process of claim 1, wherein the step of precipitating the C5 sugar using a boron capture agent comprises forming a boron-diol complex to thereby precipitate the C5 sugar.

19. The process of claim 1, wherein the step of isolating the C5 sugar from the precipitate comprises filtering the precipitate to obtain the C5 sugar in solid form.

* * * * *